United States Patent
Deng

(10) Patent No.: US 7,682,333 B2
(45) Date of Patent: Mar. 23, 2010

(54) POWERED SURGICAL HANDPIECE WITH PRECISION SUCTION CONTROL

(75) Inventor: Wenjie Deng, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 1378 days.

(21) Appl. No.: 10/047,742

(22) Filed: Jan. 15, 2002

(65) Prior Publication Data
US 2003/0135151 A1 Jul. 17, 2003

(51) Int. Cl.
*A61M 1/00* (2006.01)
(52) U.S. Cl. .................................................. 604/35
(58) Field of Classification Search ................... 604/30, 604/32, 35, 902; 606/1, 79, 80, 159, 167, 606/170, 171, 180; 251/304, 309, 98, 100, 251/180, 181, 188, 192, 208, 209, 283, 298, 251/352, 900; 403/DIG. 4; 24/572.1, 573.11
See application file for complete search history.

(56) References Cited

U.S. PATENT DOCUMENTS

| | | | | |
|---|---|---|---|---|
| 2,525,329 A | * | 10/1950 | Wyzenbeek | 604/267 |
| 4,113,288 A | * | 9/1978 | Cox | 285/148.15 |
| 4,927,116 A | * | 5/1990 | Schwarz et al. | 251/312 |
| 5,241,990 A | * | 9/1993 | Cook | 137/625.46 |
| 5,871,493 A | * | 2/1999 | Sjostrom et al. | 606/180 |
| 6,312,441 B1 | * | 11/2001 | Deng | 606/170 |
| 6,436,067 B1 | * | 8/2002 | Deng et al. | 604/32 |

OTHER PUBLICATIONS

U.S. Appl. No. 09/454,113, filed Dec. 1999.

* cited by examiner

*Primary Examiner*—Todd E Manahan
*Assistant Examiner*—Jonathan A Hollm
(74) *Attorney, Agent, or Firm*—Flynn, Thiel, Boutell & Tanis, P.C.

(57) ABSTRACT

A handpiece (20) for actuating a surgical cutting accessory (24). The handpiece has a housing (22) with a bore (46) through which a suction is drawn. A valve (50) regulates the suction flow. The valve (50), formed of metal, has an barrel (60), formed of rubber, that surrounds the rotating valve stem (56). The barrel defines a non-circular openings (96) through which there is suction flow. The openings are shaped to have small diameter sections (104) that initially come into registration with the suction bore when the stem is rotated to the open state. This ensures that, when the valve is open, there is only a relatively small surgeon-selected suction flow through the handpiece. The barrel is formed with ribs (94, 106) the serve as seals between the valve and the adjacent surface of the housing. A suction fitting (49) is rotatably fitted to the proximal end of the handpiece.

20 Claims, 11 Drawing Sheets

POWERED SURGICAL HANDPIECE WITH PRECISION SUCTION CONTROL

FIELD OF THE INVENTION

This invention relates generally to powered surgical handpieces that include conduits through which suction is drawn. More particularly, this invention relates to this class of handpiece with a valve that can be set to accurately, and with nominal ergonomic effort, regulate flow through the suction conduit.

BACKGROUND OF THE INVENTION

Endoscopic surgical procedures are routinely performed in order to accomplish various surgical tasks. In an endoscopic surgical procedure, small incisions, called portals, are made into the patient. An endoscope, which is a device that allows medical personnel to view the surgical site, is inserted in one of the portals. Surgical instruments used to perform a specific surgical task are inserted into other portals. The surgeon views the surgical site through the endoscope to determine how to manipulate the surgical instruments in order to accomplish the surgical procedure. An advantage of performing endoscopic surgery is that, since the portions of the body that are cut open are minimized, the portions of the body that need to heal after surgery are likewise reduced. Moreover, during an endoscopic surgical procedure, only relatively small portions of the patient's internal organs and tissue are exposed to the open environment. This minimal opening of the patient's body lessens the extent to which a patient's organs and tissue are open to infection.

The ability to perform endoscopic surgery has been enhanced by the development of powered surgical tools especially designed to perform endoscopic surgical procedures. One such tool, for example, is sold by the Applicant's Assignee under the trademark HUMMER TPS. This tool is in the form of a cylindrical handpiece designed to be held in the hand of the surgeon. Internal to the handpiece there is a motor. A front end of the handpiece is provided with a coupling assembly for releasably holding a cutting accessory. The types of cutting accessories that are attached to this handpiece include shavers, resectors, planers and burs. Integral with the motor and coupling assembly is a device for transmitting the rotary power developed by the motor to the cutting accessory.

The handpiece also has a suction conduit. This is because, in an endoscopic surgical procedure, irrigating fluid is introduced into the surgical site. This fluid serves as a transport media for removing debris from the surgical site. In order to remove the irrigating fluid, and the material in the fluid, a suction path is provided through the cutting accessory and the handpiece. A suction pump is connected to the handpiece and provides a suction force for drawing the fluid and material away from the surgical site. In order to control the suction flow through the cutting accessory and the handpiece, the handpiece is provided with a manually operated valve. Thus, with a single handpiece, a surgeon both manipulates the cutting accessory and controls the suction of material away from the surgical site.

For the above reasons, presently available handpieces have proven to be very useful tools for performing surgical procedures. Nevertheless, there is a limitation associated with the suction systems that are integral with these handpieces. Specifically it is very difficult for a surgeon to regulate the suction rate, the rate at which fluid and debris are drawn away from the surgical site through the handpiece. Presently available handpieces have valves that allow variable control of suction flow through the associated suction conduit.

The Applicant's U.S. patent application Ser. No. 09/454,113, filed Dec. 3, 1999, entitled POWERED SURGICAL HANDPIECE WITH SUCTION CONDUIT INCLUDING A STEPPED VALVE TO REGULATE FLOW THROUGH THE SUCTION CONDUIT, now U.S. Pat. No. 6,436,067 and incorporated herein by reference, discloses one such powered surgical handpiece with a suction valve. The handpiece of this invention includes a valve with an indexing mechanism that provides tactile feedback when the valve is in an intermediate position between its fully open and fully closed states. This handpiece thus provides a surgeon with some ability to sense the position of the suction control valve when it is between its fully open and fully closed states.

Nevertheless, there are some limitations associated with the suction control offered by available handpieces. One limitation is associated with available handpieces is that it is often difficult to set the associated valve to a position in which the valve only allows a relatively small suction to be drawn at the surgical site.

Still another disadvantage of many handpieces is that even when their suction valves are in the fully closed states, there may be some leakage suction flow. Sometimes a surgeon finds the presence of this flow distracting.

Furthermore, handpieces are typically designed so that the suction flow out of the handpiece is through a tube that is attached to the proximal end, the rear end, of the handpiece. Sometimes, if a surgeon holds the handpiece in an unusual position, this tube may bend or fold over itself. If either of these two events occur, the tube may close and, in effect, stop further suction flow from the surgical site. If this flow is blocked, the surgeon must take the time to interrupt the procedure to remove the bend in the tube so as to allow suction flow to continue. Making the surgeon perform this task interrupts his/her concentration from the actual surgical procedure and lengthens the overall time it takes to perform the procedure. The lengthening the time it takes to perform a surgical procedure runs contrary to one of the goals of modern surgical practice which is to hold the time the patient is kept under anesthesia to as short as possible.

Also, even if the tube does not fold shut, if the handpiece to which it is attached is held in an unusual position, the tube may drag across the arms or other body parts of the surgeon. This contact with the tube may interfere with the surgeon's ability to perform the desired surgical procedure or simply distract the surgeon's attention.

SUMMARY OF THE INVENTION

This invention relates to a new powered surgical handpiece with a valve that can readily be set to positions at which the valve only allows relatively small suction flows through the handpiece. The handpiece of this invention is further constructed so that, when the valve is in the closed state, there is no leakage suction flow through the handpiece. Still, another feature of this invention is that it is relatively simple ergonomically, for the surgeon to set the valve in the desired position. The handpiece of this invention is further constructed so that its valve has a minimal number of sealing components. Moreover, the handpiece of this invention is provided with a suction outlet that minimizes the likelihood that the surgeon, when manipulating the handpiece, will bend the attached suction tube into a such a position that the tube will close.

BRIEF DESCRIPTION OF THE DRAWINGS

The invention is pointed out with particularity in the claims. The above and further advantages of the invention may be better understood by reference to the following description taken in conjunction with the accompanying drawings, in which:

DETAILED DESCRIPTION

Figure 1:
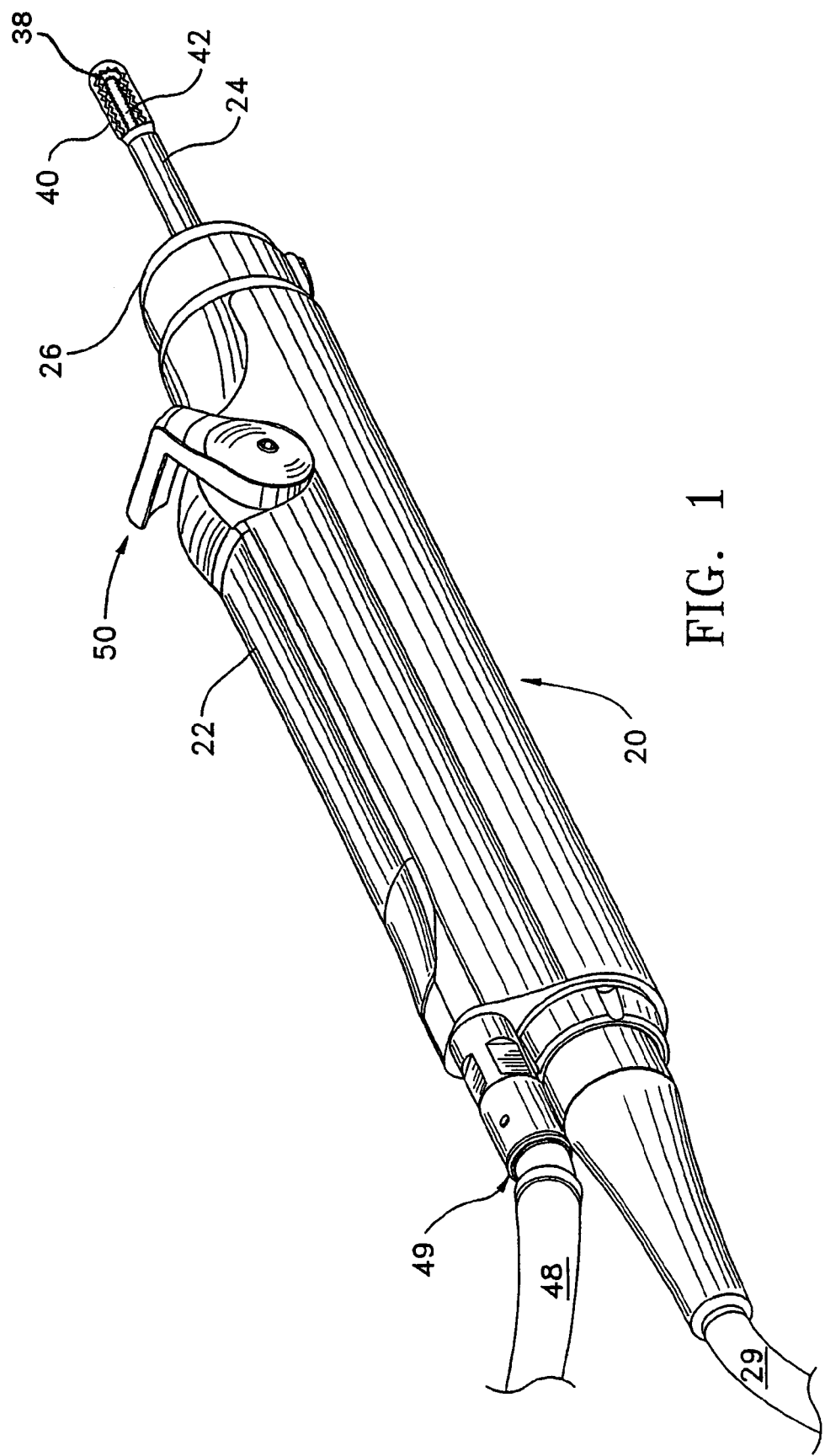
FIG. 1 depicts a powered surgical handpiece of this invention.
Figure 2:
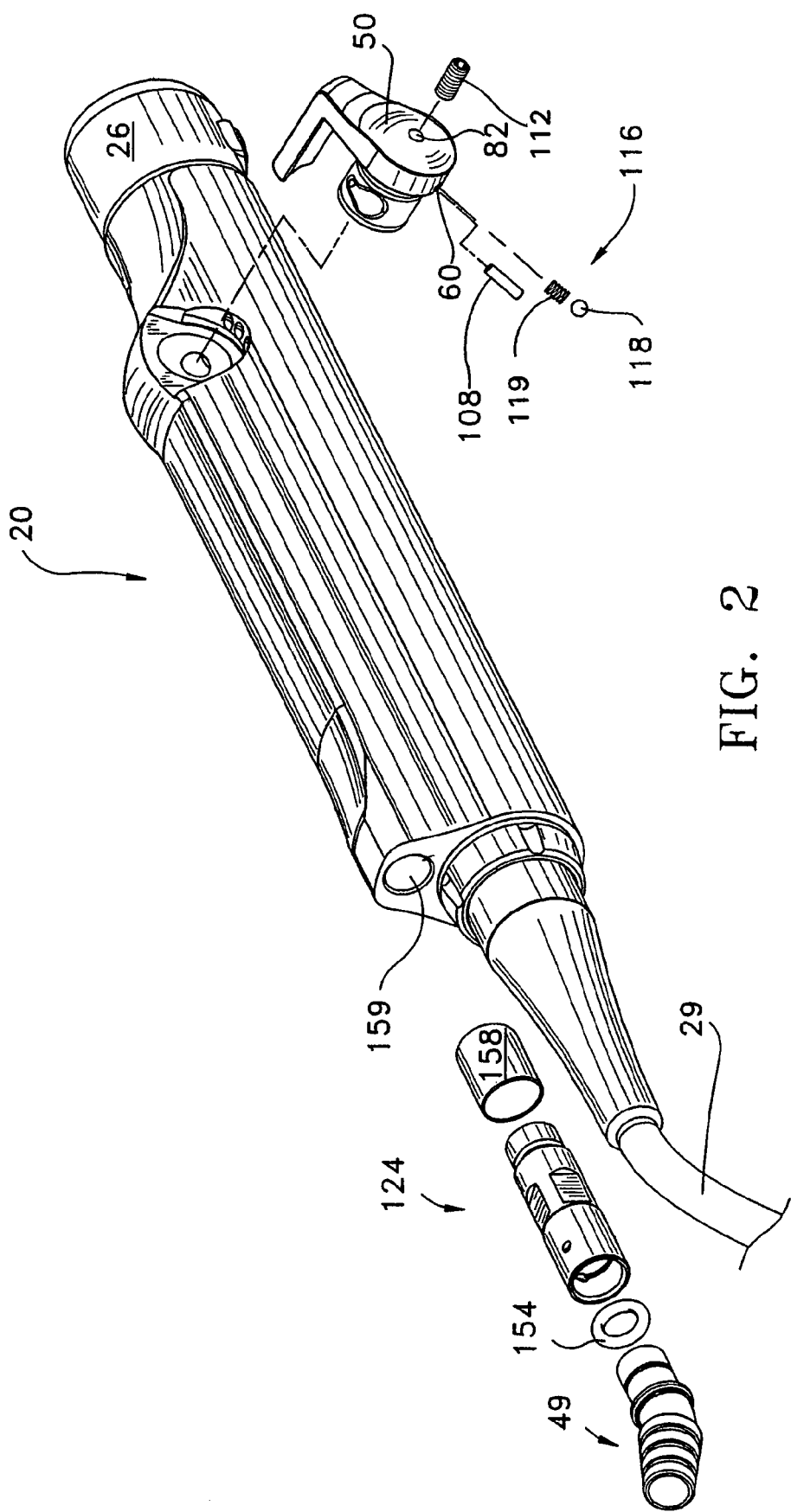
FIG. 2 is an exploded view of the surgical handpiece.

FIGS. 1 and 2 depict a surgical handpiece 20 of this invention. Handpiece 20 is designed to perform endoscopic surgical procedures though other handpieces of this invention may be designed to perform other types of surgical procedures. The handpiece 20 includes an elongated housing 22 that functions as the body of the handpiece. A complementary cutting accessory 24 is attached to the front end, also known as the distal end, of the handpiece 20. A coupling assembly 26 attached to the distal end of the housing 22 releasably couples the cutting accessory to the handpiece. A motor 28 (FIG. 3A) is located inside of the housing 22. Power is supplied to the motor from a power supply, (not illustrated), through a power cable 29 attached to the rear end, also known as the proximal end, of the housing 22.

Figure 3A:
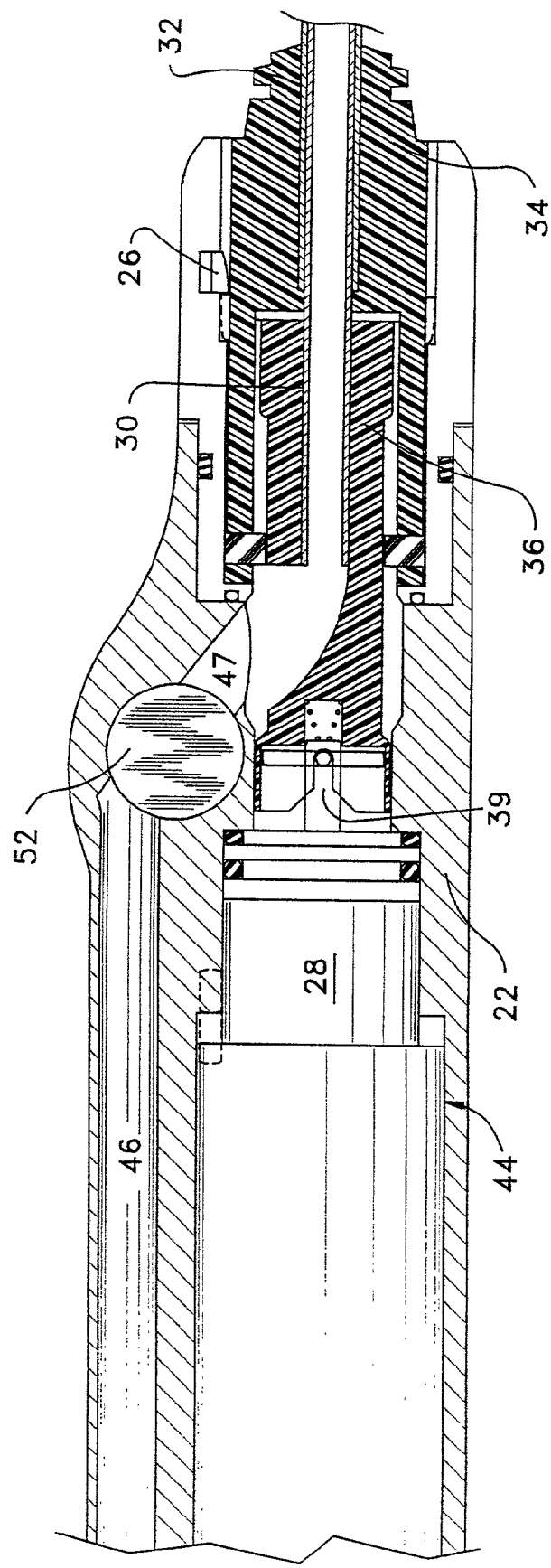
FIG. 3A is a cross sectional view of the distal end of the handpiece of this invention and of the proximal end of a cutting accessory that is coupled to the handpiece.

As seen best by FIGS. 1 and 3A, the cutting accessory 24 includes inner and outer tubes 30 and 32, respectively. A static hub 34 is attached to the proximal, rear end of the outer tube 32. The static hub 34 is held to the handpiece 20 by coupling assembly 26 so as to hold the cutting accessory 24 to the handpiece. An inner hub 36 is fixed to the proximal end of the inner tube 30. The inner hub 36 extends through the coupling assembly 26 and into the open distal end of the housing 22. Inner hub 36 engages a drive shaft 39 that extends out from the forward end of motor 28. Thus, the actuating of the motor 28 results in the rotation of inner tube 30.

Exemplary coupling assemblies that can be integrated into the handpiece 20 of this invention are disclosed in the Applicant's U.S. Pat. No. 6,312,441B1, POWERED HANDPIECE FOR PERFORMING ENDOSCOPIC SURGICAL PROCEDURES, issued Nov. 6, 2001; and the Applicant's Assignee's U.S. Pat. No. 5,192,292, SURGICAL APPARATUS USEABLE FOR ARTHROSCOPIC SURGERY, issued Mar. 9, 1993, both of which are incorporated herein by reference. It should be understood that the above are only two of many coupling assemblies that can be integrated into this invention. Coupling assemblies that use other members to both hold the static hub 34 to the handpiece and that couple the inner hub 36 to the handpiece drive shaft may be employed.

The distal end of outer tube 32 is shaped to define an opening 40. Opening 40 is the opening through which the cutting device integral with the inner tube 30 is exposed to the environment. The distal end of inner tube 30 is also formed with an opening 42. The portions of the outer and inner tubes that define openings 40 and 42, respectively, have sharp teeth, not identified. Thus, in the depicted cutting accessory 24, these teeth form the cutting member, the tissue-shaping member, of the cutting accessory. In alternative cutting accessory, a bur head may be attached to the distal end of the inner tube to function as the tissue-shaping member. In the illustrated cutting accessory 24, opening 42 is formed in the inner tube 30 at a point proximal to where bur 38 is attached to the tube. Fluid and debris from the surgical site to which the cutting accessory 24 is applied flow through openings 40 and 42 and into the center of inner tube 30.

Figure 3B:
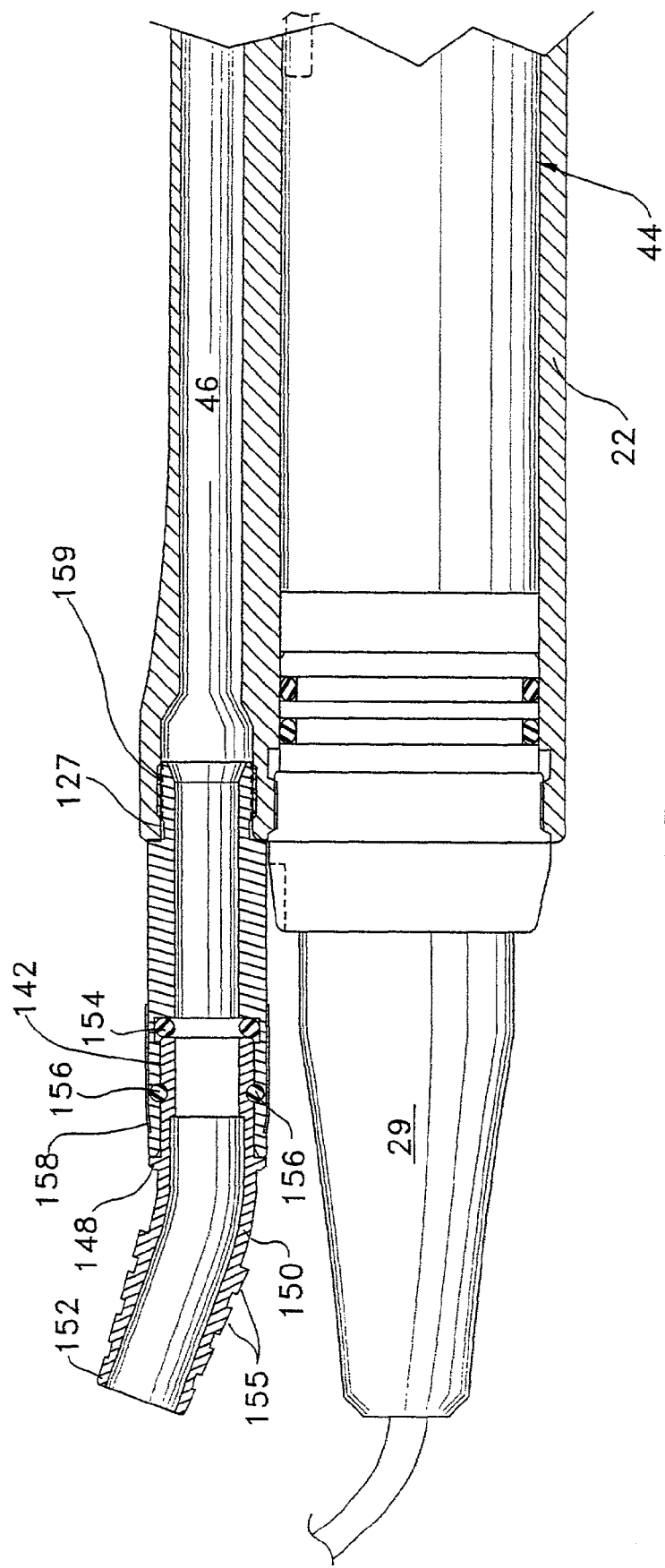
FIG. 3B is cross sectional view of the proximal end of the handpiece.

As seen best by references to FIGS. 2, 3A and 3B, the handpiece housing 22 is formed to have a large diameter main bore 44. The main bore 44 is the space in the distal end of the housing 22 in which inner hub 36 is seated. Main bore 44 also serves as the space within housing 22 in which the motor 28 and drive shaft 39 are located. Extending parallel with and located above main bore 44, the housing 22 is formed to have a suction bore 46 of smaller diameter than the main bore. A diagonally extending suction passage 47 formed in the distal end of housing 22 provides a fluid communication path from the distal end of main bore 44 to the suction bore 46. Suction bore 46 opens at the proximal end of the housing 22. Suction bore 46 is the bore through which a suction is drawn from cutting accessory openings 40 and 42 and inner tube 30. The suction is drawn through the handpiece 20 by a suction pump, (not illustrated), that is connected to the handpiece through a suction tube 48. More particularly, suction tube 48 is removably attached to a suction fitting 49 that is rotatably mounted in the proximal end of housing 22.

Flow through suction bore 46 is regulated by a valve 50. More particularly, valve 50 is rotatably mounted in a circular valve chamber 52 formed in the housing 22. In the depicted version of the invention, valve chamber 52 connects suction passage 47 to suction bore 46. The valve 50, now described by reference to FIGS. 4, 5A, 5B and 5C, includes a cylindrical valve stem 56 that is rotatably seated in the valve chamber 52. Valve stem 56 is formed to have a bore 58 that extends from side-to-side through the stem. A valve barrel 60 is molded over the circumferential surface of the valve stem. The valve barrel 60 also extends through the stem bore 58. The portion of the valve barrel 60 extending through the stem bore 58 defines a valve bore 62. Valve bore 62 is the conduit that is selectively placed in registration with suction passage 47 and suction bore 46 to allow suction flow through the handpiece 20. Integral with valve stem 56, valve 50 is formed to have a valve arm 64. Arm 64 is the exposed portion of the valve 50 that is manually set to position the valve stem 56.

More particularly, it will be observed that the valve stem 56 is shaped to have a main section 66 that has a first outer diameter. At the end of the main section 66 located away from the valve arm 64, valve stem 56 has a first recessed section 68 with an outer diameter less than that of the main section 66. Stem bore 58 it will be observed extends through stem main section 66 and an adjacent portion of the first recessed section 68. Stem bore 58, it will be further observed, has an oval shape. A circular end plate 70 is located next to and is integral with first recessed section 68. End plate 70 has an outer diameter greater than that of the stem main section 66.

Valve stem 56 is further formed to have a second recessed section 72 that extends from main section 66 towards arm 64. Second recessed section 72 has the same outer diameter as first recessed section 68. The valve stem 56 also has a base plate 74 located between the adjacent surface of valve arm 64 and the second recessed section. Base plate 74 has the same outer diameter as end plate 70. Owing to the different diameters of the different sections of the valve stem 56, it will be observed that there are circumferential slots 76 located above recessed sections 68 and 72.

Valve arm 64 includes a circular base 80 that is the portion of the arm from which stem base plate 74 extends. A threaded bore 82 extends inward from the outer face of base 80. Bore 82 is aligned with the center axis of base 80 that is also the rotatational axis of valve stem 56. Base 80 is further formed to have a bore 84 that extends upwardly from the bottom of base 80 and that intersects bore 82. A third bore, bore 86, is further formed in the base to extend inwardly from the outer perimeter of the base 80. The purposes of bores 82, 84 and 86 are explained below.

The valve arm 64 is further formed to have a projecting lever 88 that extends upwardly from base 80. Lever 88 has an end section 90 that extends over the valve stem 56.

Valve barrel 60 both defines valve bore 62 and a set of ribs that are integral with the valve 50. The ribs, as will be discussed later, function as seals. The valve barrel is formed from a rubber such as the fluorine-containing hydro-carbon polymer synthetic rubber sold under the trademark Viton by the DuPont Company of Wilmington, Del. In more preferred versions of this invention, this material has a low friction filler such as 10% fluorine polymer filler sold under the trademark Teflon by the DuPont Company. Alternatively, the valve barrel may be manufactured from silicon rubber. In one preferred method of assembling the handpiece 20 of this invention, after the valve member is shaped, valve barrel 60 is molded over the valve stem 56. While not illustrated, it should be understood that as a result of this molding process annular rings of the material forming the barrel 60 flow into the circumferential slots 76 located adjacent the opposed ends of the stem main section 66. These rings, as well as the portions of the material that flows into bore 58, hold the barrel to the valve stem 56. The barrel is molded the valve stem so as to only cover the stem main section 66 and first and section recessed sections 68 and 72, respectively.

Figure 4:
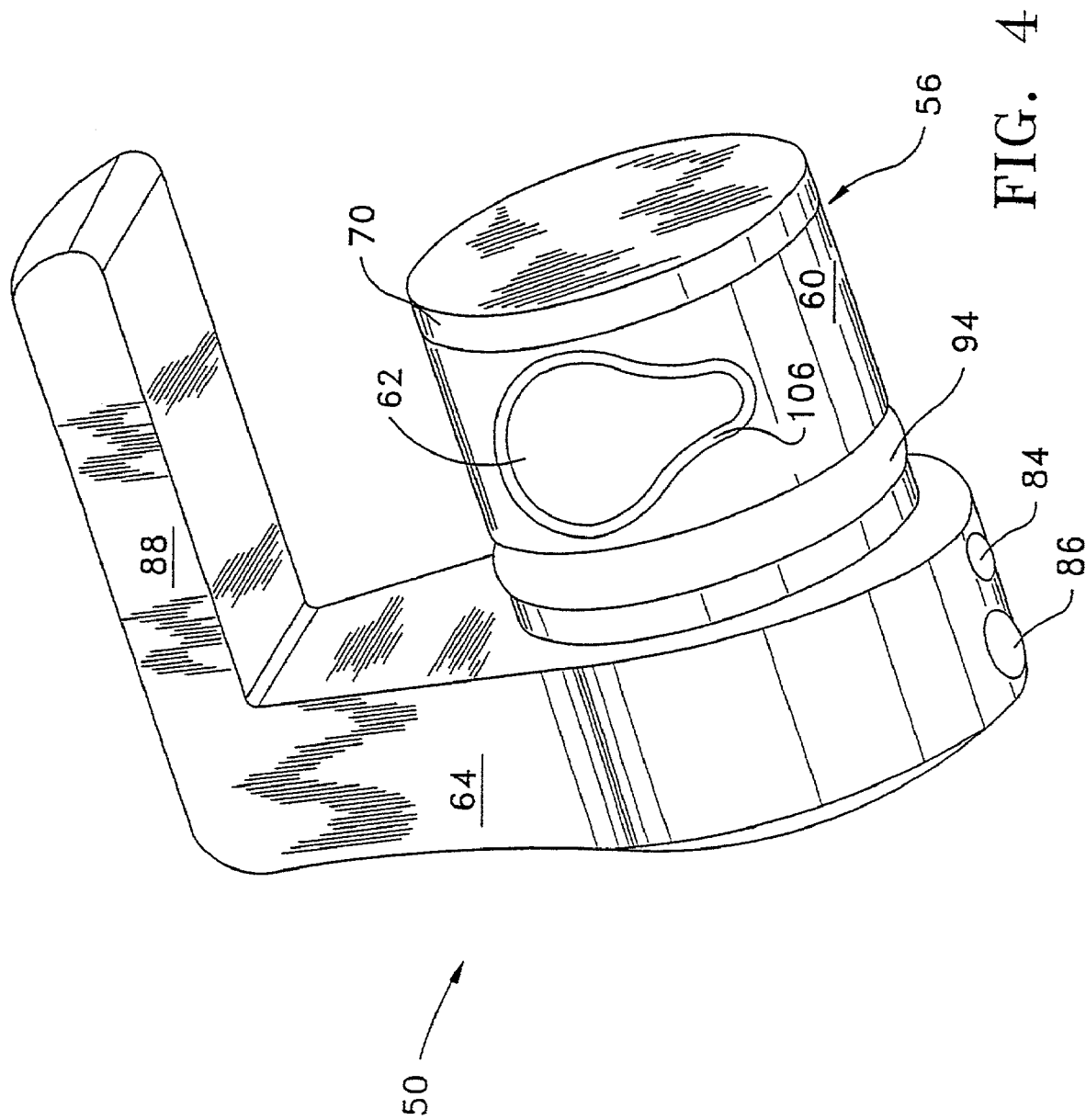
FIG. 4 is a perspective view of the suction valve with molded barrel of this invention.
Figure 5C:
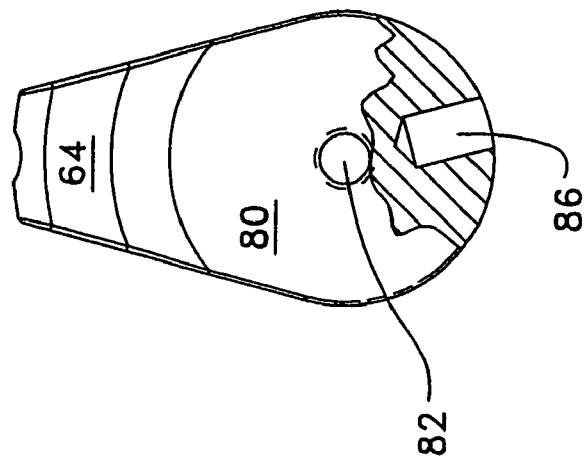
FIG. 5C is a plan and partially cutaway view of the suction valve taken along line 5C-5C of FIG. 5A.
Figure 5B:
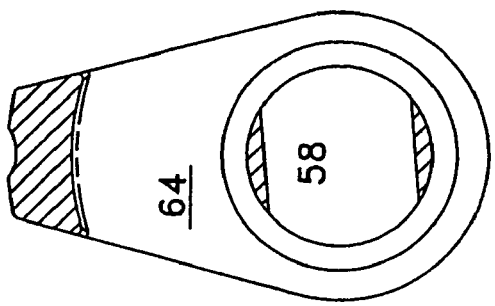
FIG. 5B is a plan and partially cutaway view of the side face of the suction valve taken along line 5B-5B of FIG. 5A.
Figure 5A:
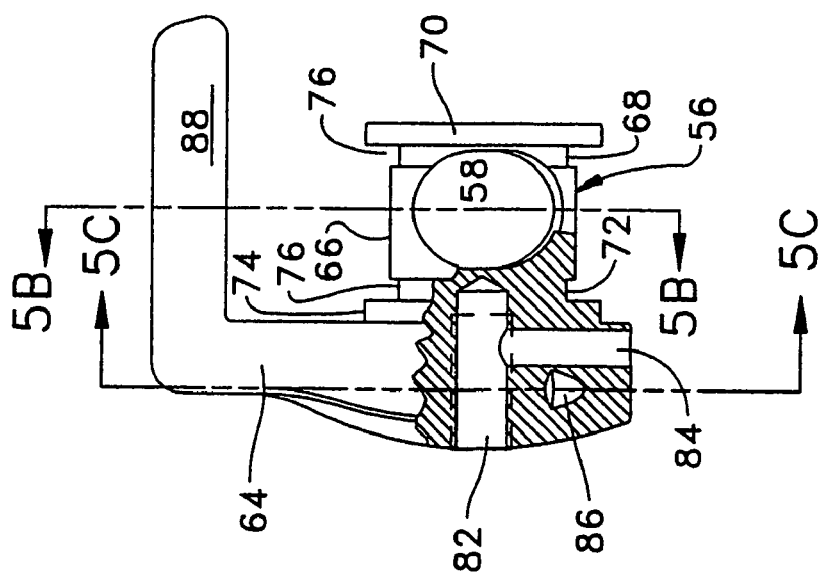
FIG. 5A is a plan and partially cutaway view of the front of the suction valve.
Figure 6:
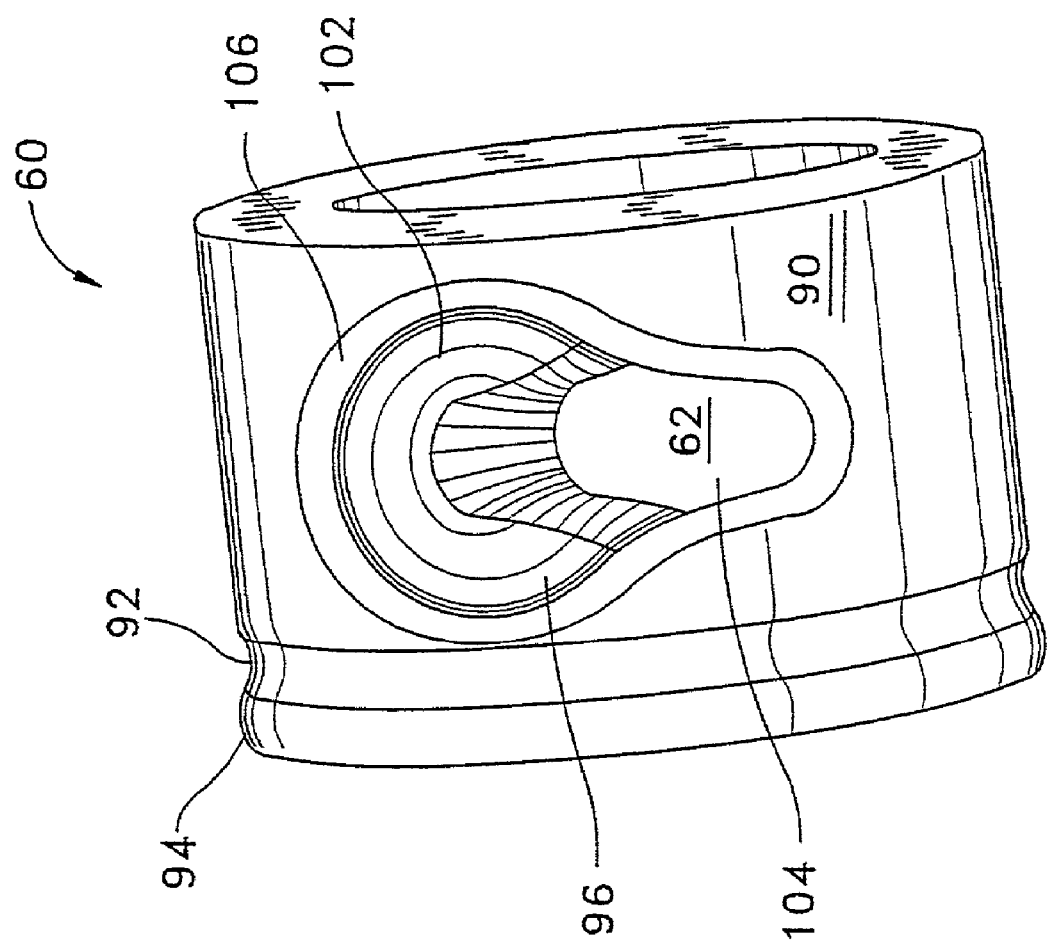
FIG. 6 is a perspective view of the valve barrel.

As seen best in FIGS. 4 and 6, valve barrel 60 is molded to have a generally cylindrical outer surface 90 that surrounds the stem main section 66. The valve barrel 60 is molded so that outer surface 90 is flush with the adjacent exposed outer perimeter of end plate 70. Extending towards the valve arm 64, the valve barrel is first shaped to have an annular groove 92 that is recessed relative to outer surface 90. The outer end of the valve barrel, the portion that abuts base plate 74, is shaped to define a rib 94 that rises above outer surface 90 and that extends circumferentially around the valve stem 56. More specifically, rib 94 is dimensioned to have an outer diameter that is between 0.001 and 0.012 inches larger than the diameter of valve chamber 52. For example, in one particular version of the invention, valve chamber 52 has a diameter of 0.438 inches; the valve barrel 60 is shaped so that rib 94 has an outer diameter of 0.444 inches.

The portion of the barrel 60 in stem bore 58 defines the valve bore 62. Bore 62 is shaped so that its openings 96 are non-circular. In the depicted version of the invention the openings into bore 62 are of teardrop or keyhole shape. That is the opening has a first large diameter section 102 that has a large-circular profile. The bore 62 is further formed so that section 102 tapers into a smaller diameter second section 104. Valve barrel 60 is further formed so that the bore openings 96 are in opposite orientation on either side of the valve stem 56. Thus, in FIG. 6, the depicted opening 96 is shaped so that large diameter section 102 is located towards or at the top of the page and small diameter section 104 is directed towards the bottom of the page. If one were to look at the opposite side of the valve depicted in FIG. 6, it would be noted that the small diameter section 104 of the opening 96 depicted in FIG. 6 is opposite and oriented toward the top of the page. The companion opening large diameter section 102 is directed towards the bottom of the page. Thus, the opening at the opposite side of valve barrel 60 is identical to the opening 96 shown in FIG. 6, but is reversed by being reoriented 180°.

The valve barrel 60 is further formed so as to define a rib 106 around the outer perimeter of each bore opening 96. Ribs 106 project above barrel outer surface 90. More specifically, ribs 106 are formed so that their outer surfaces are on a circle that has a diameter greater than the diameter of valve chamber 52. In most preferred versions of the invention, the ribs 106 are formed so that their outer surfaces are within a circle that has a diameter 0.001 to 0.010 inches greater than the diameter of the chamber 106 in which the valve 50 is seated. For example in one version of the invention, the valve chamber has a diameter of 0.438 inches. In this version of the invention, valve barrel outer surface 90 has a diameter of 0.436 inches and the barrel is further shaped so that the outer surfaces of ribs 106 are on a circle that has a diameter of 0.444 inches.

Figure 7:
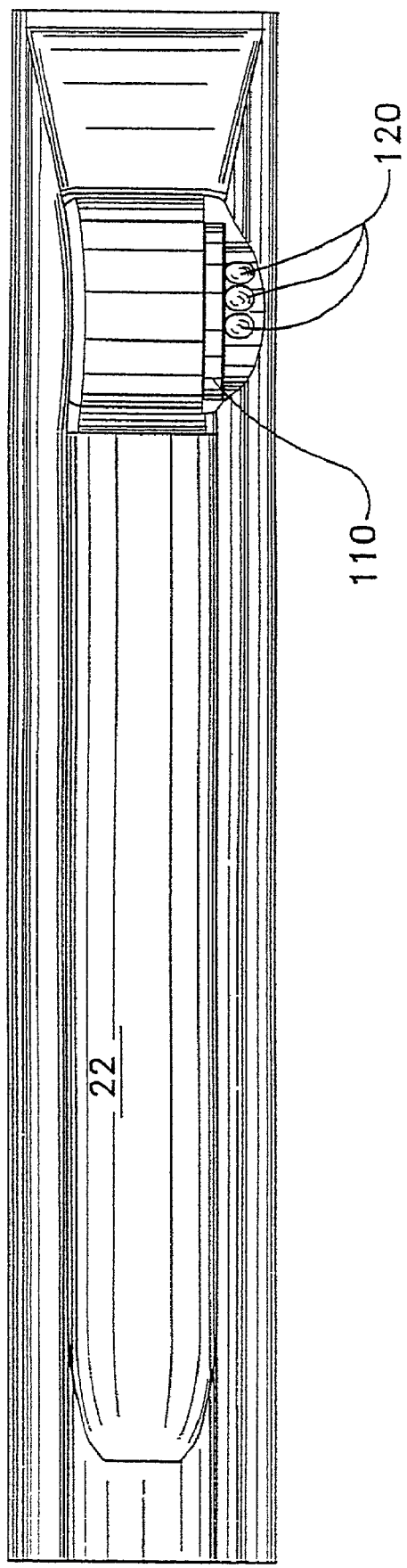
FIG. 7 is a top view of the handpiece housing.

Valve 50 is releasably held to housing 22 by a retaining pin 108 as best understood by reference to FIGS. 2, 4 and 7. Specifically, the retaining pin 108 is slidably fitted in bore 84 formed in the valve arm 64. An end of the pin 108 extends out of bore 84 and seats in an arcuately shaped groove 110 formed in the outer surface of the housing 22 adjacent the valve chamber, (FIG. 7). Pin 108 has an overall length that is slightly less than the combined length of bore 84 and the depth of groove 110. In order to fit the valve 50 to the rest of the handpiece 20, both the housing 22 and valve are inverted. When the valve 50 is positioned so that bores 82 and 84 are upwardly directed, pin 108 is slip fitted in bores 82 and 84. When the valve 50 is so positioned pin 108 is wholly fitted in both bores 82 and 84. With the housing 22 and valve 50 in the inverted states, the valve is seated in valve chamber 52. When the valve 50 is so seated, pin 108 aligns with groove 110. The righting of the handpiece 20 causes the pin 108 to drop into groove 110. The seating of pin 108 in groove 110 rotatably holds the valve 50 to the housing. As pin 108 seats in groove 110, the end portion of the pin 108 in bore 82 drops out of that bore 82. A set screw or pin 112 is then secured in bore 82. Set screw 112 covers the end of bore 84 that opens into bore 82. The set screw 112 thus prevents the pin 108 from sliding into bore 82 to such an extent that the free end of the pin retracts out of groove 110. Thus, set screw 112 holds pin 108 in groove 110 so that the pin holds the valve 50 to the housing 22.

The handpiece 20 of this invention has an indexing assembly 116 to facilitate the tactile-controlled setting of valve 50 by the surgeon. The indexing assembly 116, now described by reference to FIGS. 2, 4 and 7, includes a ball 118 that is seated in the open end of valve bore 86. A spring, 119 fitted in the base of bore 86, exerts an outwardly directed force on the ball 118. Thus, when the valve 50 is coupled to the housing 22, ball 118 is urged against the outer surface of the housing.

The housing 22 is shaped so that the arcuate surface of the housing against which ball 118 abuts is shaped to have three notches 120. The notches 120 are in the form end slices of sphere and are dimensioned to accommodate an end portion of ball 118.

Figure 8:
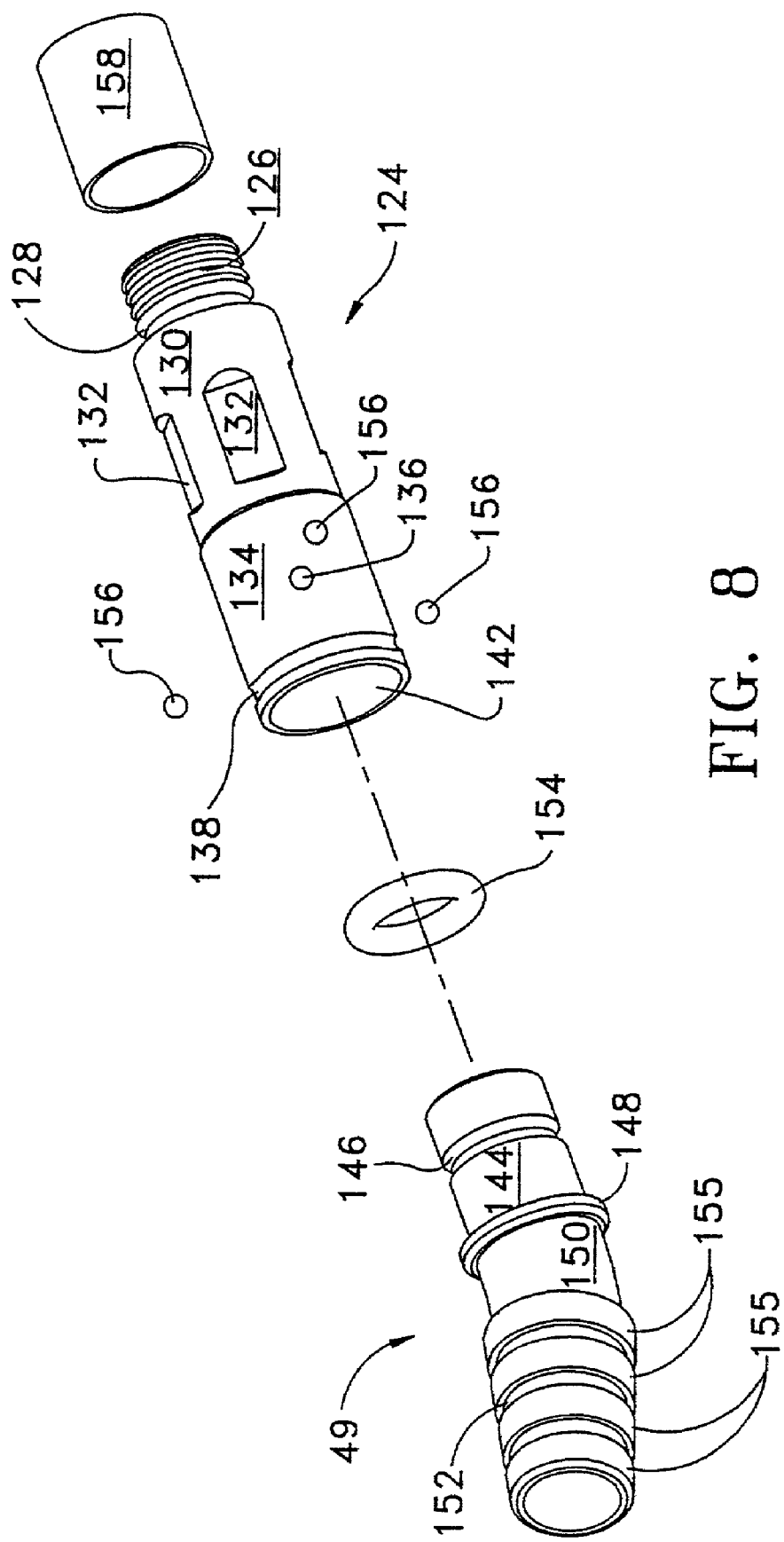
FIG. 8 is an exploded view of the suction fitting the components that rotatably hold the suction fitting to the rest of the handpiece.

The suction fitting 49, as seen by reference to FIGS. 2, 3B and 8, is rotatably secured to a suction mount 124 that extends rearwardly from the proximal end opening of the housing suction bore 46. The suction mount 124 is a generally tubular shaped member formed from stainless steel or other appropriate material. The suction mount 124 is shaped to have a distal end head 126 with a circular outer surface. More particularly, the suction mount head 126 is provided with threading, (not identified,) so that the suction mount can be screw secured in the proximal end of the suction bore 46. Extending proximally from the head 126, suction mount 124 has a neck 128 with an outer diameter less than that of the head. Housing 22 is formed to have a circumferential lip 127 that projects into the open distal end of the suction bore 46. Consequently, when the suction mount 124 is threaded into bore 46, housing lip 127 seats around mount neck 128 to hold the suction mount in place.

Located proximally from neck 128, the suction mount 124 has a main section 130. Main section 130 is shaped to have an outer surface that is primarily circular and further shaped to have an outer diameter greater than that of suction mount head 126. Nevertheless, it will be observed that four flats 132 are formed in the main section 130 (two flats shown). The flats 132 serve as grasping surfaces against which a wrench can be placed to secure the suction mount 124 in the housing 22. A base section 134, located rearwardly of main section 130 forms the proximal end of the suction mount 124. Base section 134 has a circular outer diameter that is greater than the outer diameter of the main section 130. The base section 134 is further formed to have three holes 136 that are spaced equangularly apart from each other around a common circle (one hole 136 shown). The suction mount 124 is further formed so that there is a groove 138 that extends circumferentially around the outside of base section 134 a short distance forward of the proximal end of the suction mount.

A bore 140 extends axially through the suction mount. Bore 140 is of constant diameter. However, it will be observed that there is a larger diameter counterbore 142 within suction mount base section 134.

The suction fitting 49 has cylindrical head 144. This head 144 is designed to be slip fitted in and rotate within suction mount counterbore 142. A groove 146 with a semi-circular cross sectional profile extends circumferentially around the outer surface of head 144. Suction fitting 49 is further formed so as to have an annular flange 148 that is located around the proximal end of the head 144. Flange 148, it will be observed, extends outwardly beyond the outer surface of head 144.

Suction fitting 49 is further formed to have a curved neck 150 that extends rearwardly from the proximal end of head 144. A straight tail 152 extends rearwardly from the proximal end of neck 150. A set of tapered spaced apart barbs 155 are integrally formed with the outer surface of tail 152. Barbs 155 are the surfaces over which the suction tube 48 is fitted. Neck 150 is curved so that the angle between the longitudinal axes of fitting head 144 and fitting tail 152 is between 10 and 40°. In more preferred versions of the invention, this angle is between 15 and 25°.

Prior to inserting the suction fitting head 144 into the suction mount 124, a compressible O-ring 154 is lodged in the base of mount counterbore 142. When the suction fitting head 144 is seated in the counterbore 142, O-ring 154 is compressed between the mount and the suction fitting to form a seal around the head 144. Also, as part of the assembly process, the suction fitting head 144 is fitted in the suction mount base section 134 so that head groove 146 is aligned with base section holes 136. A ball bearing 156 is fitted in each hole 136 so as to seat in groove 146. The ball bearings 156 thus rotatably hold the suction fitting 49 to suction mount 124.

Once the suction fitting 49 is mated to the suction mount 124, a retention sleeve 158 is fitted over the mount base section 134 over holes 136. The proximal end of the retention sleeve 158 is crimped down into suction mount groove 138 to hold the sleeve in place. Owing to the position of the sleeve 158 over holes 136, the sleeve holds the ball bearings 156 in the holes and against the suction fitting 49. Once the suction fitting is coupled to the suction mount 124, the suction mount head 126 is threaded in a counterbore 159 in the proximal end of housing suction bore 46, (counterbore threading not shown).

Suction flow is controlled with the surgical handpiece of this invention by the setting of valve 50. When the valve 50 is in the closed state, the forward facing end of valve bore is not in registration with the distal end of suction passage 47. Thus, the valve blocks suction through from the distal end of the handpiece 20 and cutting accessory 24. Moreover, given the dimension of barrel ribs 106 relative to the valve chamber 52, when the valve stem and barrel are seated in the valve chamber, the ribs 106 are compressed against the inner wall of the housing 22 that defines the valve chamber 52. Ribs 106 thus prevent leakage suction flow around the interstitial gap between valve 50 and the adjacent inner surface of the handpiece housing 22.

In one preferred version of the invention, valve 50 is designed so that the valve 50 is in the closed state when the valve arm 64 is in its most proximal oriented position. Thus, valve 50 is opened by pushing forward on lever 88. The rotation of valve stem 56 thus places valve bore 62 in registration with both suction passage 47 and suction bore 46. Initially, owing to the shape of valve bore 62, only the smaller diameters sections 104 of the bore openings 96, the sections that define relatively small openings, comes into registration with the proximal end of the suction passage 47 and the distal end of the suction bore 46. Thus, when the valve is initially opened, the valve only allows a relatively small suction flow to be drawn therethrough.

The suction flow is increased by pivoting the valve arm 64 forward. This motion places the large diameter sections 102 of the valve bore openings 96 in registration with the suction passage 47 and suction bore 46. This increases the size of the opening through the valve so as to increase the suction that is drawn through the handpiece 20.

Another feature of the invention is that as the valve is actuated, ball 118 sequentially moves in and out of housing notches 120. The seating of the ball 118 in the notches places a small resistance on the movement of the valve that can be manually overcome. Nevertheless, this resistance serves as tactile feedback for the surgeon's setting the position of the valve. In many preferred versions of the invention, housing 22 is shaped so that one of the notches 120 is positioned to receive the ball 118 when it is the small diameter section 104 of the valve bore openings 96 that are primarily in registration with the suction bore 46 and suction conduit 47. This construction thus provides tactile feedback to the surgeon that the valve is set in a position in which it only allows minimal suction flow through the handpiece 20.

The handpiece of this invention is further constructed so that the valve lever/the valve barrel are typically rotated 85° or less to be moved from its fully closed state to its fully opened state. In more preferred versions of the invention, the valve lever/the valve barrel are rotated 80° or less to be moved from the fully closed to the fully opened states. In still more preferred versions of the invention, the valve lever and the valve barrel are rotated 75° or less to move the valve between the fully opened and closed states. A benefit of this feature is that it means the arm lever only has to be moved a relatively short arcuate distances to set the valve to the desired flow state.

Furthermore, the handpiece 20 can be constructed so that the valve arm 64 does not have to be rotated more than 45° from a centerline that extends perpendicular to the longitudinal axis of the handpiece 20 in order to fully open or close the valve 50. Thus, the surgeon does not engage in significant ergonomic stress when he/she extends and retracts his/her finger in order to set the valve state. For example, in one preferred version of the invention, the handpiece 20 is assembled so that the fully opened and full closed states of the valve are located at asymmetric positions relative to the centerline of the valve chamber 52 that extends from a perpendicular to the longitudinal axis of the handpiece. Specifically, the valve is constructed so that valve lever 88 has to only be rotated 30° back from the centerline in order to fully close the valve and 45° forward from this centerline in order to place the valve in the fully open state.

It should be understood that, in order to so construct the handpiece of this invention so that the valve barrel does not have to be rotated through a relatively large angular arc in order to be moved from between its fully open and fully closed states, it may be necessary to make the valve barrel and stem relatively large. For example, in one version of the invention, the cross sectional diameter of the suction passage and suction bore openings that open into the valve chamber are 0.166 inches. In this version of the invention, the outer diameter of the portion of the valve barrel 60 that defines the valve bore 62 is at least 0.400 inches. In more preferred versions of the invention, the outer diameter of this portion of the valve assembly is at least 0.430 inches. It should also be recognized that valve 50 has a single valve arm 64.

Still another feature of the handpiece of this invention is that, when the valve is fitted to the housing 22, rib 94 is compressed against the perimeter surface of the housing 22 that defines the open end of the valve chamber 52. Thus, rib 94 functions as the sleeve that prevents leakage of fluid out of the valve chamber 52. When the rib 94 is so compressed, a portion of the material forming the rib extends outwardly. The portion of this material within the valve chamber 52 seats in the space defined by barrel groove 92.

Thus, the handpiece 22 of this invention provides suction flow that can be selectively set to a low flow rate or a high rate, a valve 50 for setting the suction flow that is ergonomically easy to use and compact in size, tactile feedback of the valve when it is a number of different positions and that does not require a significant number of components to assemble.

The handpiece 20 of this invention is further provided with a suction fitting 49 that rotates relative to the handpiece housing 22. Owing to the bend in the fitting neck 150, the suction tube 48 attached to the handpiece extends away from the longitudinal axis of the handpiece housing 22. Collectively, these features of the invention reduce the likelihood that the suction tube can inadvertently fold over itself and close so as to block suction flow. Moreover, these features of the invention also minimize the likelihood the, the surgeon, when manipulating the handpiece 20, will drag the suction tube 48 across portions of his/her body. The elimination of the tube-against-surgeon contact eliminates the chance that such contact will be disconcerting to the surgeon and interrupt his/her concentration.

Figure 9:
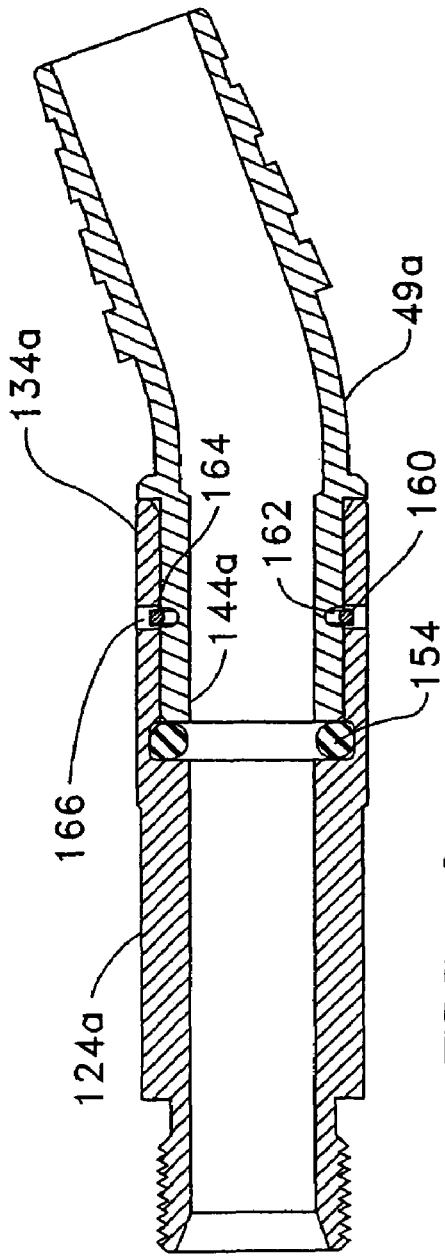
FIG. 9 is a cross sectional view of an alternative sub-assembly for rotatably securing the suction fitting to a complementary suction mount.

FIG. 9 illustrates an alternative suction mount-and-suction fitting sub-assembly of this invention. The depicted suction mount 124a is not provided with holes for accommodating ball bearings. Instead suction mount is formed so that inner wall of the base section 134a is formed with an annular groove 160 that is contiguous with counterbore 142.

The head 144a of the complementary suction fitting 49a is provided with a groove 162 having the same width of groove 160. When suction fitting head 144a is seated in counterbore 142, a C-shaped retaining ring 164 rotatably holds the suction fitting 49a to the suction mount 124a. More particularly, the lock ring 164 is seated in both suction mount groove 160 and suction fitting groove 162 to rotatably hold the suction fitting to the suction mount. At least three small bores 166 are formed in the mount base section 134a and open into groove 160. Bores 166 thus allow a tool to be inserted in the suction mount 124a so as to compress the lock ring 164 so to make it possible to remove the suction fitting 49a form maintenance.

An advantage of the foregoing assembly is that it eliminates the need to provide the previously described retaining sleeve.

Figure 10:
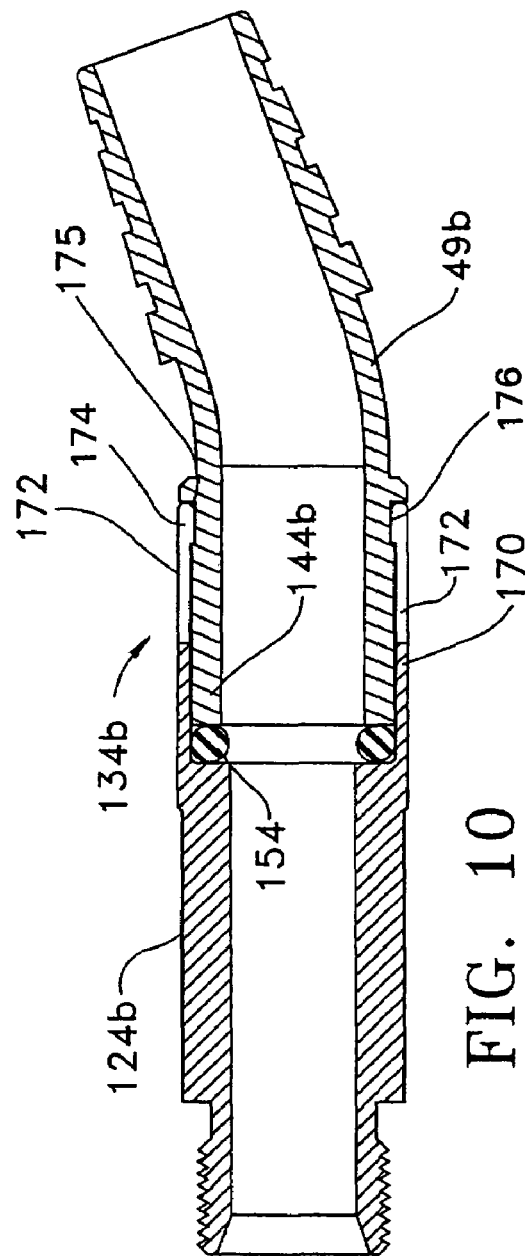
FIG. 10 is a cross sectional view of a second alternative sub-assembly for rotatably securing the suction fitting to a complementary suction mount.

A second alternative suction mount-and-suction fitting sub-assembly is now described by reference to FIG. 10. Suction mount 124b of this version of the invention is not provided with a base section that is completely solid therearound. Instead, base section 134b has a distal portion 170 adjacent main section 130b. This distal portion 170 is generally tube-like in shape. A plurality of fingers 172 extend proximally from distal section 170. Each finger 172 is generally arcuate in cross sectional shape. Suction mount 124b is formed so that each finger 172 has at its proximal end a tab 174 that extends inwardly toward the center axis of the suction mount. It will further be observed that the inner corner edge 175 of each finger, the edge that defines a corner of the complementary tab 174, is beveled.

The complementary suction fitting 49b fitted to suction mount 124b is formed to have a rectangular groove 176 that extends circumferentially around the outer surface of its head 144b. Groove 176 is located adjacent flange 148b and is designed to accommodate finger tabs 174.

Suction fitting 49b is coupled to suction mount 124b by inserting head 144b between fingers 172 and into base distal section 170. Since the metal forming the fingers 172 has some flexibility, the fingers flex outwardly to accommodate the insertion of the suction fitting head 144b. When the suction fitting head is fully inserted, the finger tabs 174 are in registration with and seat in groove 176. The fingers 172 thus hold the suction fitting 49b to the suction mount 124b so that suction fitting 49b is able to rotate relative to the mount 124b.

An advantage of the foregoing version of the invention is that it does not require any supplemental components to hold the suction fitting 49b to the suction mount 124b. A disadvantage is that it may be difficult, if not impossible, to flex the fingers away from the fitting head 144b in order to remove the suction fitting from the suction mount for maintenance.

It should be understood that the foregoing description has been limited to particular versions of this invention. It will be apparent that modifications can be made with the attainment of some or all of the advantages thereof. For example, there is no obligation that each handpiece of this invention include both the valve assembly that provides precision control of suction through the handpiece and the suction fitting 49 that rotates relative to the handpiece housing 22.

Also, various features of the invention may have constructions that are different from what has been described. For example, in the described version of the invention, notches 120 in which indexing ball 118 seats abut each other. In alternative versions of the invention, these notches may be spaced from each other. Also other versions of the invention may have less or more notches 120 than the three notches illustrated.

Furthermore, alternative indexing assemblies may be integrated into the surgical handpiece of this invention. Thus, it may desirable to provide an indexing assembly with a member that is mounted to the handpiece housing 22 and directed towards the valve 50. This member would be against surface indentations defined by the valve to provide tactile-feedback inducing resistance to the manual actuation of the valve.

Figure 11:
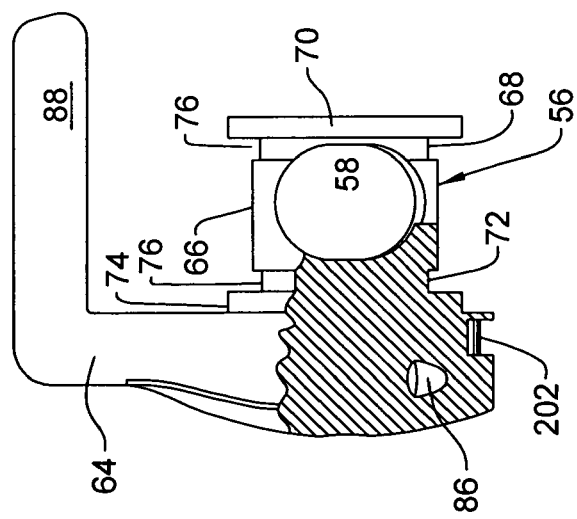
FIG. 11 is a plan and partially cutaway view of the front of a second suction valve.
Figure 12:
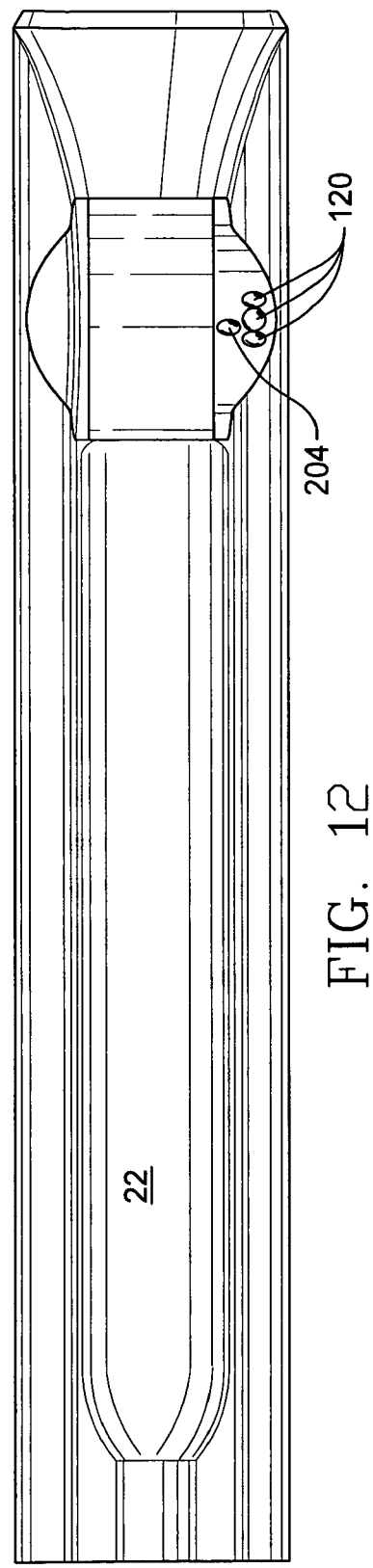
FIG. 12 is a top view of a second handpiece.

Moreover, alternative assemblies for removably holding the valve 50 to the housing 22 may be employed. For example, instead of mounting a pin in the valve, a retaining member may be mounted in the handpiece housing, such as in hole 204 shown in FIG. 12. This member would engage a surface groove 202 of the valve shown in FIG. 11 to removably hold the valve to the housing. The retaining member would be movably fitted to the housing, if not removable, to facilitate the removal and reinstallation of the valve.

It should similarly be recognized that the valve may have constructions different from what has been illustrated. For example the valve may be shaped so that the openings into and out of the valve bore have geometries different from what has been described. Nevertheless, it is believed that, for many optimal constructions of the invention, the valve bore openings will have shapes that are non-circular. For example, in some versions of the invention, the valve bore openings, relative to circle in which the valve stem rotates, may be linear. In these versions of the invention, the opposed sides of the bore openings, from the end that first registers with the suction bore may taper away from the centerlines of the openings. In still other versions of the invention, the valve bore openings may be defined by both curved and straight line segments that collectively define a first narrow width opening and then a second wider width opening.

Also, there is no requirement that all versions of the invention have the described molded-in-place valve barrel. In alternative versions of the invention, this barrel can be eliminated. If this version of the invention is constructed it is, however, typically necessary to provide an O-ring about the outer end of the valve stem 56. In order to provide a seal between the interstitial space between the outer surface of the valve stem and the adjacent inner wall of the housing 22 it would then be necessary to mount some type of sealing strips to the surface of the valve stem.

Alternatively, the valve barrel may simply be in the form of a tube of material that defines the valve bore and the seals around the openings into the bore. In these versions of the invention, the sleeve may be molded as a separate component. Then, as part of the handpiece assembly process, this sleeve is fitted into a bore formed in the valve stem.

Furthermore, alternative means may be provided to rotatably mount the valve to the handpiece housing 22. Thus in some version of the invention, the valve chamber may be a section of a through bore that extends between opposed sides of the housing. In these versions of the invention, seals and arms may be attached to both sides of the valve stem in order to both hold it in place and prevent leakage from the handpiece.

Moreover, alternative means may be provided to rotatably mount the suction fitting 49 to the handpiece housing 22. For example, in some versions of the invention, it may not be necessary to rotatably mount the suction fitting to a suction mount that is, in turn, attached to the housing 22. In these versions of the invention, the suction fitting may be directly rotatably mounted to the housing 22. This could be accomplished by mounting a version of lock ring 164 in a complementary groove formed in the housing 22 that is contiguous with the suction bore 46. Alternatively, set screws removably fitted to the suction mount or the proximal end of the housing may seat in fitting groove 146 so as to removably, rotatably hold the fitting to the housing.

Also, while the described handpiece includes an electrically-driven motor for actuating the cutting accessory 24 other versions of the invention may have other power producing devices. For example, in some versions of the invention, the handpiece may have a pneumatically driven motor. Alternative devices for actuating a cutting accessory include light emitting devices such as lasers, ultrasonic generators and radio signal (radio frequency) generators.

Similarly, the material from which the components of this invention are made are likewise be understood to be exemplary and not limiting. Rigid material other than the disclosed stainless steel may be used to manufacture the valve 50. Compressible material other than the disclosed material may be used to fabricate the valve barrel 62.

Therefore, it is an object of the appended claims to cover all such variations and modifications that come within the true spirit and scope of this invention.

What is claimed is:

1. A surgical handpiece for actuation of a cutting accessory attached to said handpiece, said handpiece comprising:

a housing shaped to define a suction bore that extends from the cutting accessory and a valve chamber that intersects the suction bore;

a power generating unit disposed in said housing for actuating the cutting accessory;

a valve assembly, said valve assembly including:

a valve stem rotatably mounted in the valve chamber, said valve stem being formed from rigid material and being shaped to have a valve stem bore that extends between openings formed in said valve stem, the valve stem bore having a cross sectional area; and a valve barrel formed of compressible material and disposed in the valve stem bore, said valve barrel being shaped to define a valve bore that extends through the valve stem bore, the valve bore having opposed valve bore openings and a cross sectional area less than the cross sectional area of the valve stem bore, said valve barrel being formed to define first and second ribs, each said rib extending around an outer perimeter of a separate one of the valve bore openings and being dimensioned to contact a surface of said housing that defines the valve chamber; and an arm attached to said valve stem that is located outside of said housing.

2. The surgical handpiece of claim 1, wherein said valve barrel is further formed to define a third rib that extends circumferentially around said valve stem and that is dimensioned to contact the surface of said housing that defines the valve chamber.

3. The surgical handpiece of claim 1, wherein said valve barrel has a portion disposed in said valve stem bore and another portion which extends around the outer surface of said valve stem, said valve barrel having a third rib that extends circumferentially around said valve stem and that is dimensioned to contact the surface of said housing that defines the valve chamber and to define a groove that extends circumferentially around said valve stem, the groove being located adjacent said third rib.

4. The surgical handpiece of claim 1, wherein:
said housing is formed so that the valve chamber is a closed bore that has a base defined by an inner surface of said housing;
said valve stem is formed with an end surface that is located adjacent the inner surface of said housing that defines the base of the valve chamber; and
said valve barrel having a portion disposed in said valve stem bore and another portion which extends circumferentially around said valve stem.

5. A surgical handpiece for actuation of a cutting accessory attached to said handpiece, said handpiece comprising:
a housing, said housing formed to define a suction bore that extends from the cutting accessory and a suction passage;
a power generating unit disposed in said housing for actuating the cutting accessory;
a valve assembly, said valve assembly including:
 a valve chamber defined by said housing between the suction bore and the suction passage; and
 a valve rotatably mounted in the valve chamber and including a movable control member disposed outside of said housing, said valve comprising a valve stem formed from rigid material and further shaped to have a stem bore that extends therethrough, and a valve barrel formed of flexible material and having a portion which extends through the stem bore so as to define a valve bore that extends through said valve barrel with first and second non-circular valve bore openings at the opposite ends of said valve bore, wherein the first valve bore opening is selectively placed in registration with the suction bore and the second valve bore opening is placed in registration with the suction passage as the valve is rotated from a closed state to a fully open state, the first valve bore opening being shaped to have a first narrow width section that is first placed in registration with the suction bore during the rotation of the valve from the closed state to the fully open state and a second, wide width section that is placed in registration with the suction bore as said valve is further rotated toward the fully open state, the second valve bore opening being shaped to have a first narrow width section that is first placed in registration with the suction passage during the rotation of the valve from the closed state to the fully open state and a second, wide width section that is placed in registration with the suction passage as the valve is further rotated toward the fully open state.

6. The surgical handpiece of claim 5, wherein said valve barrel defines a rib that is located around a perimeter of each said valve bore opening, each said rib being positioned to extend away from said valve stem and being dimensioned to abut a surface of said housing that defines the valve chamber.

7. The surgical handpiece of claim 5, wherein said valve barrel is further formed to have a circular rib that extends circumferentially around said valve stem, said rib being dimensioned to extend away from said valve stem and to abut a surface of said housing that defines the valve chamber.

8. The surgical handpiece of claim 5, further including an indexing assembly attached to said valve assembly and said housing for providing a resistance to the rotation of said valve when said valve is rotated to a position in which the first narrow width section of the first valve bore opening is placed in partial registration with the suction bore.

9. The surgical handpiece of claim 8, wherein:
said housing is formed so that the valve chamber comprises a closed bore that has a base defined by an inner surface of said housing;
said valve is formed with an end surface that is located adjacent the inner surface of said housing that defines the base of the valve chamber; and
a retaining member is positioned in one of said valve and said housing and is positioned to engage the other one of said housing and said valve to removably hold said valve in the valve chamber.

10. The surgical handpiece of claim 5, wherein said first and second valve bore openings are identically shaped but inverted relative to one another on opposite sides of said valve such that said first narrow width section of said first valve bore opening is disposed circumferentially adjacent said second wide width section of said second valve bore opening, and said second wide width section of said first valve bore opening is disposed circumferentially adjacent said first narrow width section of said second valve bore opening.

11. A surgical handpiece for actuation of a cutting accessory attached to said handpiece, said handpiece comprising:
a housing, said housing being formed to define a suction bore that extends from the cutting accessory and a valve chamber that intersects the suction bore;
a power generating unit disposed in said housing for actuating the cutting accessory;
a valve assembly, said valve assembly including:
 a valve stem formed from rigid material and moveably mounted in the valve chamber, said valve stem being formed to define a stem bore that extends through said valve stem;
 a valve barrel comprising flexible material and having a portion disposed within the stem bore so as to define a valve bore, said valve bore having a non-circular valve opening that is selectively placed in registration with the suction bore, said valve opening having a first section with a first cross sectional width and a second section contiguous with the first section and having a second cross sectional width that is greater than the first cross sectional width, such that when said valve stem is moved from a closed position to an open position, the first section of the valve opening moves into registration with the suction bore before the second section of the valve opening moves into registration with the suction bore; and
 a moveable control member connected to said valve stem that is located outside of said housing for manually establishing the position of said valve stem.

12. The surgical handpiece of claim 11, wherein said valve stem is rotatably moveable in the valve chamber.

13. The surgical handpiece of claim 12, further including an indexing assembly secured to said valve assembly and said housing for providing a set resistance to the rotation of said valve stem when said valve stem is rotated to a position in which the first section of the valve bore opening is placed in partial registration with the suction bore.

14. The surgical handpiece of claim 11, wherein said valve barrel is further formed to define a first rib that is located around a perimeter of the valve opening and dimensioned to contact a surface of said housing that defines the valve chamber.

15. The surgical handpiece of claim 14, wherein said valve barrel is further formed to have a second rib that extends circumferentially around said valve stem, said second rib being dimensioned to contact the surface of said housing that defines the valve chamber.

16. A surgical handpiece for actuation of a cutting accessory attached to said cutting accessory, said handpiece comprising:
- a housing, said housing shaped to have a suction bore that extends from the cutting accessory and a valve chamber that intersects the suction bore;
- a power generating unit disposed in said housing for actuating the cutting accessory; and
- a valve assembly, said valve assembly including:
  - a valve stem rotatably mounted in the valve chamber, said valve stem being formed from rigid material and being shaped to have an outer surface and a valve stem bore that extends through said valve stem;
  - a valve barrel located around the outer surface of said valve stem, said valve barrel being shaped to define a first rib that extends circumferentially around said valve stem, and second and third ribs that extend around opposed openings of a valve bore, said first, second and third ribs being dimensioned to abut surfaces of said housing that define the valve chamber; and
  - a lever attached to said valve stem that is located outside of said housing.

17. The surgical handpiece of claim 16, wherein:
said valve stem bore has a cross sectional area; and
said valve barrel includes a portion disposed inside the valve stem bore, said portion defining the valve bore and being shaped to have a cross-sectional area less than a cross sectional area of the valve stem bore.

18. A surgical handpiece for actuation of a cutting accessory attached to said handpiece, said handpiece comprising:
- a housing formed to define a suction bore that extends from the cutting accessory and a valve chamber that intersects the suction bore, the valve chamber being a closed-ended bore;
- a power generating unit disposed in said housing configured to actuate the cutting accessory;
- a valve assembly, said valve assembly including:
  - a valve body that is rotatably fitted in the valve chamber and defined by a stem and a lever integral with said stem, the stem being shaped to define a through bore that is selectively placed in registration with the suction bore, said valve body being formed with a first hole that is directed towards said housing and a second hole having a portion that intersects the first hole; and
  - a first pin that is slidably fitted in the first hole and the portion of the second hole that intersects the first hole, and a second pin that is removably fitted in the second hole, wherein said second pin is dimensioned so that said second pin seats in the portion of the second hole in which said first pin can slide, and said first pin is dimensioned so that when said second pin is disposed in the portion of said second hole in which said first pin can slide, said first pin is blocked from sliding in the second hole and extends out of said first hole and engages a surface of said housing.

19. The surgical handpiece of claim 18, wherein said valve body is formed with a third hole, and an indexing member is fitted in the third hole and positioned to engage a surface of said housing.

20. The surgical handpiece of claim 18, wherein:
said stem is formed from rigid material;
said valve body including a valve barrel formed from compressible material and having a portion which extends through the through bore of said stem and defines a valve passage, the valve passage having opposed passage openings, and said valve barrel is further formed to define ribs that are located around the outer perimeters of the passage openings, the ribs being dimensioned to abut surfaces of said housing that define the valve chamber.

* * * * *

UNITED STATES PATENT AND TRADEMARK OFFICE
CERTIFICATE OF CORRECTION

PATENT NO. : 7,682,333 B2 Page 1 of 1
APPLICATION NO. : 10/047742
DATED : March 23, 2010
INVENTOR(S) : Wenjie Deng It is certified that error appears in the above-identified patent and that said Letters Patent is hereby corrected as shown below:

Column 13, line 3: replace "stern" with --stem--.

Column 15, line 34: replace "cross sectional" with --cross-sectional--.

Signed and Sealed this

First Day of June, 2010

David J. Kappos
*Director of the United States Patent and Trademark Office*